United States Patent [19]

Johnson

[11] 4,200,056
[45] Apr. 29, 1980

[54] SEGMENTED PLATEN FOR APPLYING LIQUIDS TO A FLAT SURFACE

[75] Inventor: Leighton C. Johnson, Edwardsburg, Mich.

[73] Assignee: Miles Laboratories, Inc., Elkhart, Ind.

[21] Appl. No.: 760,857

[22] Filed: Jan. 21, 1977

[51] Int. Cl.² ............................................. B05C 5/02
[52] U.S. Cl. ................................... 118/401; 118/423
[58] Field of Search ....................... 118/401, 412, 423; 8/3, 94.11; 427/2, 4

[56] References Cited

U.S. PATENT DOCUMENTS

| | | | |
|---|---|---|---|
| 1,112,960 | 10/1914 | Adams et al. | 118/412 |
| 2,573,952 | 11/1951 | Bretherton | 118/412 |
| 2,800,418 | 7/1957 | Cannon | 118/412 X |
| 3,431,886 | 3/1969 | McCormick et al. | 118/401 X |

*Primary Examiner*—John P. McIntosh
*Attorney, Agent, or Firm*—Roger N. Coe

[57] ABSTRACT

A platen and the method of operation thereof are described for applying liquid to a generally flat surfaced object, such as a microscopic slide, so as to provide multiple liquid treatments in at least two transverse bands across the width of the object. The apparatus and method permit different biological markers to be applied to separate areas of the same specimen on a microscopic slide; the same biological marker to be applied to different specimens on the same microscopic slide; the same biological marker to be applied to separate areas of the same specimen on a microscopic slide; or different biological markers to be applied to different specimens on the same microscopic slide.

10 Claims, 5 Drawing Figures

SEGMENTED PLATEN FOR APPLYING LIQUIDS TO A FLAT SURFACE

FIELD OF THE INVENTION

The present invention relates to a system for applying liquid to a generally flat surface of an object and, more particularly, to a segmented platen and method for rapidly and evenly applying multiple liquid treatments to one surface of a microscopic slide. Still more particularly, the invention relates to apparatus and method for staining a plurality of seriate microscopic slides with multiple biological markers applied in at least two transverse bands across the width of each slide.

BACKGROUND OF THE INVENTION

For purposes of microscopic examination of certain material, particularly cellular materials such as blood, tissue and the like, it is customary to place a smear of a liquid or substrate containing the material (e.g., a smear of plasma containing blood cells), or a thin section of the material itself (e.g., a thin slice of animal or plant tissue) on a transparent plate or slide. Thereafter, the material is stained by subjecting it to contact with solutions which stain or dye only certain constituents of the material or cells and this provides a contrast which facilitates visual examination.

Various staining procedures are utilized to produce different effects. For example, a solution can be employed to color a transparent substrate and thus provide contrast to essentially colorless cells; other solutions can be utilized to effect color differences between various parts of the cell. Solutions can be used to stain only portions of a cell, e.g., the nuclei and not the cytoplasm. In a procedure known as negative staining the cells can be caused to appear colorless against a colored background. Certain procedures are relatively simple and require the use of only a few solutions. Others, however, are complex and require successive applications of relatively large numbers of solutions.

In many of these staining procedures, certain of the solutions merely prepare or fix the substrate, whereas the actual stains are made by one or more natural or synthetic dyes. The dyes selected are, of course, suited for the type of cell and the staining desired. The oxazine dyes, the triphenylmethane dyes and the thiazine dyes are examples of some families of dyes that are commonly used.

In a conventional staining procedure it has been the general practice to dip the slide successively into a series of containers holding different solutions, the slide being allowed to remain in each solution for a predetermined time interval of perhaps several minutes before removing and dipping the slide into a succeeding solution. Usually the last container holds a wash, such as water, after which the slide is desired for examination. These operations can be performed manually by a technician or in automated equipment which has been developed for such operations.

Depending upon the nature of the material being stained and the type of staining desired, as many as twelve solutions are sometimes required in the overall procedure. The fact that many solutions are frequently involved merely multiples the problems. Furthermore, when successive slides are passed through the same container of solution, as in the case where dipping is employed, there is a danger of contamination of the solution. The danger increases when the same solution is used in different staining procedures for different types of materials and substrates.

In another system microscopic slides are stained by dripping stain onto the surface of a slide. Buffer is then added and an air jet is used to mix the buffer and stain on the surface of the slide. Obviously, very careful regulation of the air jet is essential in order to obtain an even distribution and mixing of buffer and stain.

In U.S. Letters Pat. No. 3,431,886 apparatus is described for automatically applying a single liquid or multiple liquids to the bottom face of a generally horizontally disposed slide while the slide is being conveyed in spaced relation over and generally parallel with a flat liquid-applying surface. The HEMA-TEK ® apparatus described in the patent and sold by Miles Laboratories, Inc. of Elkhart, Ind. has now become an industry standard for applying one or more liquids to a slide. The apparatus and system for applying liquids disclosed in U.S. Letters Pat. No. 3,431,886 is hereby incorporated by reference.

For certain purposes, however, even further control of the application of liquids to slides has been desired and it has also been desired to increase the speed at which slides are stained by automated equipment. Instead of applying only one biological marker to the full length of a slide it has now been found that with specially designed platens several treatments in transverse bands across the width of the slide are possible. This not only permits different biological markers to be applied to separate areas of the same specimen on the same slide, the same biological markers to be applied to different specimens located in separate areas of the same slide and the same biological marker to be applied to separate areas of the same specimen on a slide, but also different biological markers to be applied to different specimens located in separate areas of the same slide.

SUMMARY OF THE INVENTION

An object of the present invention is to provide an improved platen and system for treating one surface of a generally flat object with multiple liquids.

Another object of the present invention is to provide an improved platen and system for automatically and successively applying biological markers to materials carried on a plurality of slides.

Still another object of the present invention is to provide an improved platen for automatically staining separate and distinct areas of a slide by successively effecting contact between said areas and each of a plurality of solutions in such a manner as to achieve rapid and substantially simultaneous staining of the separate areas.

A further object of the present invention is to provide an improved apparatus for applying several liquid treatments in transverse bands across the width of a microscopic slide using a specially designed segmented platen.

Another object of the present invention is to apply the same biological marker to separate areas of a specimen on a microscopic slide.

Yet another object of the present invention is to apply different biological markers to separate areas of a specimen on a microscopic slide.

Still another object of the present invention is to apply the same biological marker to different specimens located in different areas of a microscopic slide.

Yet another object of the present invention is to apply different biological markers to different specimens located in different areas of a microscopic slide.

In accordance with the present invention a segmented platen and the method of operation thereof are described for applying biological markers to flat-surfaced objects, such as microscopic slides, in transverse bands across the width of such objects as the objects are conveyed along said platen. Thus, at least one liquid can be applied to separate areas of a generally flat surfaced object as that object is moved along a predetermined path in spaced generally parallel relation above a platen, said platen comprising a plurality of spaced apart segments having substantially coplanar flat upper surfaces and arranged in at least two spaced apart rows and being provided with liquid supply orifices at selected locations in said upper surfaces thereof. The segmented platen permits the same or different biological markers to be applied along each of about two to about six different platen rows to separate areas of an object, such as a microscopic slide. In addition the separate areas of said object can be exposed for the same or different periods of time to the biological markers.

Thus, different biological markers can be applied to separate areas of the same specimen on a slide; the same biological marker can be applied to different specimens located in different areas of the same slide; the same biological marker can be applied to separate areas of the same specimen on a slide; or different biological markers can be applied to different specimens located in different areas of the same slide. The use of a segmented platen apparatus not only provides adaptability to a wide variety of different programs, but permits a significant increase in the speed at which specimens can be treated with multiple biological markers since the multiple biological markers can be applied substantially simultaneously. The throughput for a given period of time can be further increased in accordance with another embodiment of this invention by utilizing microscopic slides of reduced width.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Very generally, the present invention relates to platens and a method useful for applying multiple liquid solutions to one face or surface of a generally flat-surface object. The apparatus is particularly useful for staining between about two and about six discrete areas of material carried on one face of each of a plurality of seriate microscopic slides.

Specifically, the present invention permits different biological markers to be applied to separate areas of the same specimen on a slide; the same biological marker to be applied to different specimens on the same slide; the same biological marker to be applied to separate areas of the same specimen on a slide; or different biological markers to be applied to different specimens on the same slide. The biological markers as referred to herein include any chemical or biological material that will react in some measurable fashion on the cellular level. Such biological markers can include dyes, antibodies, antigens, enzymes, antisera, fluorescent dyes, conjugated antisera, chemical reagents, enzyme substrate, nuclear substrate, and the like.

It will be understood that the platens of the present invention have particular application in automatic staining apparatus such as that described in U.S. Pat. No. 3,431,886. Such apparatus basically consists of a structural housing which contains slide conveying means for conveying slides over a particular platen, fluid storage means for storing treating fluid used to treat the slides, pumps to pump the treating fluid to treating stations on the platen and a programmer for controlling the movement of the slides and the supply of the treating fluids. Since details concerning the conveying means, the pumping means, the treating fluids and the programming of such apparatus are not essential for an understanding of the present invention, these details have been omitted from the drawings.

Figure 1:
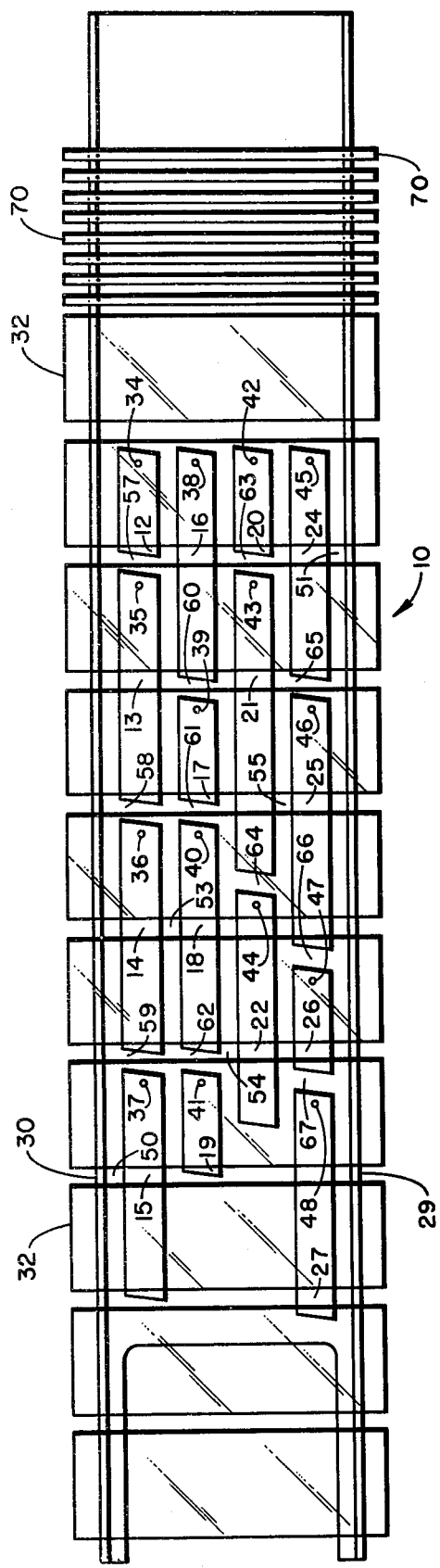
FIG. 1 is a top view of a segmented platen arranged in four rows in accordance with one embodiment of the present invention which can be used to apply liquid treatments to four discrete areas on a microscopic slide.

In the embodiment illustrated in FIG. 1, a segmented platen (10) is provided which comprises a plurality of flat liquid-applying stationary platen segments (12) to (27), securely mounted within a recess portion between parallel rails (29) and (30). In FIG. 1 the individual platen segments are spaced apart by channels into four rows generally parallel with rails (29) and (30), with platen segments (12) to (15) in the first row, platen segments (16) to (19) in the second row, platen segments (20) to (23) in the third row, and platen segments (24) to (27) in the fourth row. The upper or liquid-applying surfaces of the platen segments are substantially coplanar and are positioned parallel with and spaced closely subjacent to the plane of the upper surface of rails (29) and (30) so as to be parallel with and in close proximity to the lower face of slides (32—32) supported by rails (29) and (30) and positioned thereover.

Each platen segment can be provided with at least one orifice, such as orifices (34) to (48), through which a predetermined quantity of liquid biological markers can be injected into the space between the liquid-applying surface of a given platen segment and the overlying slide to thereby contact the lower surface of the slide and the material carried thereby with biological marker. Since the lower faces of the slides are in close proximity to the liquid-applying surfaces of underlying platen segments, e.g., a spacing of a few thousandths of an inch (i.e., 5 to 12 thousandths of an inch), the surface tension of the injected liquid is sufficient to completely fill the laminar volume between said slide and platen surfaces so that the lower surface areas of the slides are brought into contact with the liquid biological markers used.

The platen segments are preferably formed from a unitary member having channels, recesses or grooves (50) and (51) separating the first row of platen segments from rail (30) and the fourth row of platen segments from rail (29), respectively. In addition, channels, recesses or grooves (53), (54) and (55) separate the first row from the second row of platen segments, the second row from the third row of platen segments and the third row from the fourth row of platen segments, respectively. The platen segments in each row are also separated by recesses or grooves (57) to (67), substantially perpendicular to rails (29) and (30), which define platen segments of varying lengths. Recesses or grooves (57) to (67) can be at a slight angle, i.e., an angle other than 90° with rails (29) and (30), such that a diagonal wiping action occurs across a slide when the slide passes from one platen segment to another, with excess liquid passing into the channel, recess or groove.

It will be understood that the platen segments, rather than being formed from a unitary member, can be individual members suitably attached to a base member to form the desired configuration. If desired, other recess portions or grooves can be present in the segmented platen. A purpose of such recess areas or grooves is to remove excess liquid. The number, size and specific locations of such grooves will vary depending on the particular staining or liquid-applying procedures being employed. These are apparatus variations readily determinable by one skilled in the art.

It will be understood that any number of platen segments and orifices can be provided and that the number shown is only illustrative of particular staining procedures. In carrying out the Wright procedure for staining blood smears using the apparatus, for example, staining liquid can be applied at orifice (42) in platen segment 20. A buffer liquid mixed with stain by suitable means, such as a mixing coil (not shown), is immediately applied at orifice 43 in platen segment 21, and a washing liquid is applied at orifice (44) in platen segment 23.

The variation in length of platen segments permits variation in the time period during which treatment with biological markers occurs. Treatment fluid, i.e., biological markers, need not be supplied through every orifice. The presence of a number of orifices and platen segments provides a high degree of flexibility to the system and hence permits treatment of specimens with a wide variety of different treatment alternatives. State of the art electronic control on movement, pumping, and timing can be applied to achieve the permutations of each alternative. For example, objects to be treated can be advanced along the segmented platen continuously, as set forth in U.S. Letters Pat. No. 3,431,886, or intermittently in a manner set forth in U.S. application Ser. No. 730,864 filed Oct. 8, 1976, now abandoned and assigned to Miles Laboratories, Inc., which patent and application are hereby incorporated by reference. Helical conveyor elements can be used for advancing generally flat objects, such as transparent glass sides (32—32) over the platen segments as one face of each slide is automatically subjected to contact with metered quantities of liquid supplied through one or more of the orifices. Liquid can be supplied by suitable pumping means, e.g., peristalic pumps and a decade stepper or microprocessor can be used to obtain the desired motion of objects across the platen. As previously indicated, the means for advancing objects to be treated, the means for supplying fluid to the orifices and the timing means are not part of the present invention and accordingly have not been illustrated in the drawings.

To provide a compact apparatus capable of handling a fairly large number of slides, the feed mechanism should be designed to accept a large number of slides. One way this can be accomplished is by aligning slides in generally parallel face-to-face relationship with each slide disposed so as to rest upon a longitudinal edge and thereby lie in a generally vertical plane. As slides, such as slides (70—70), are advanced by the feed mechanism they are tilted forward so as to eventually lie flat and be aligned in generally parallel spaced edge to edge relationship in a generally horizontal plane, such as slides (32—32), as they pass over the liquid-applying orifices of the platen segments. After biological markers have been applied to the slides they are washed and moved beyond the platen segments (by means not shown). If desired, washing liquid can be supplied through the final orifice of each platen segment row.

Rails (29) and (30) are spaced horizontally a distance less than the length of a standard glass slide. Conventionally, a glass slide is about three inches in length and about one inch in width. Rails (29) and (30) can be formed from separate bars or rods or from the same "U" or "I" shaped channel member. In a standard operation of this type, the slides straddle or span rails (29) and (30) with each rail engaging each slide at a point spaced inwardly from an end thereof. Slides are advanced along rails (29) and (30) in such a way as to maintain a predetermined spacial relationship between the slides. Rails (29) and (30) are preferably made from a material which withstands wear against glass, such as chrome plated stainless steel, hard coated aluminum and the like. Hard coatings are prepared using high current densities and low temperature electrolytes to produce finishes of greater thickness and density than conventional anodic coatings.

Figure 2:
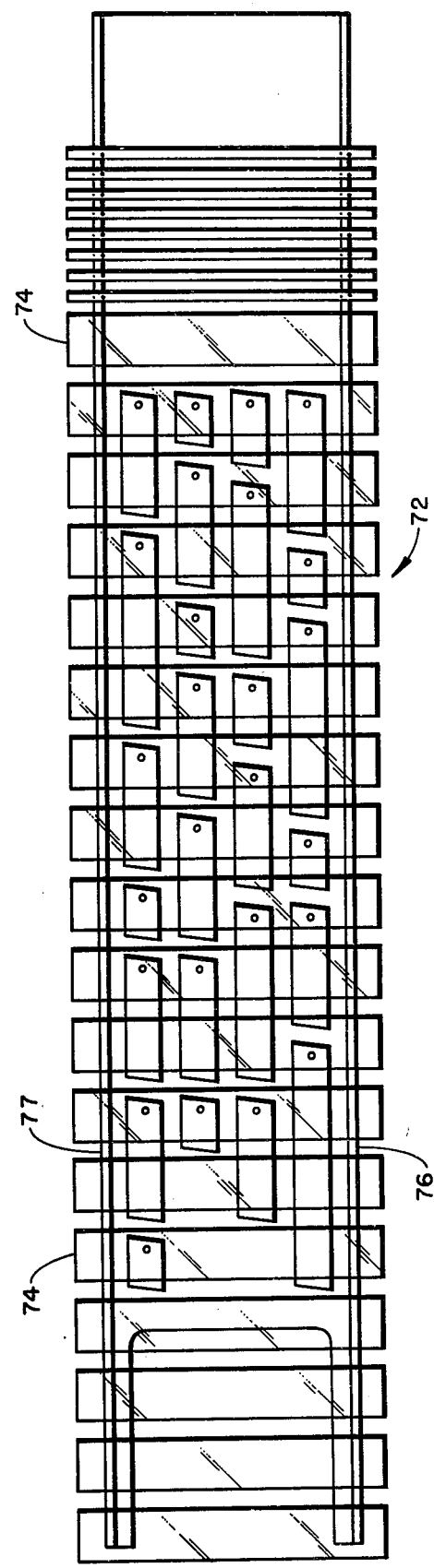
FIG. 2 is a top view of a segmented platen similar to that of FIG. 1 shown with microscopic slides of approximately half the width of conventional microscopic slides.

Using the platen of FIG. 1 to apply four liquid treatments to four discrete areas on one slide requires a liquid volume of approximately 40 microliters of reagent to fill the capillary gap between each platen segment and the overlying slide. By utilizing microscopic slides of about one half the width of a conventional slide only about 20 microliters of reagent is required at each orifice. Such an arrangement is illustrated, for example, in FIG. 2 where platen (72) has four rows of platen segments aligned generally as in FIG. 1 with slides (74—74), half the width of the slides shown in FIG. 1, resting on rails (76) and (77). This permits almost twice the throughput (compared to the platen of FIG. 1) for a given period of time.

Figure 3:
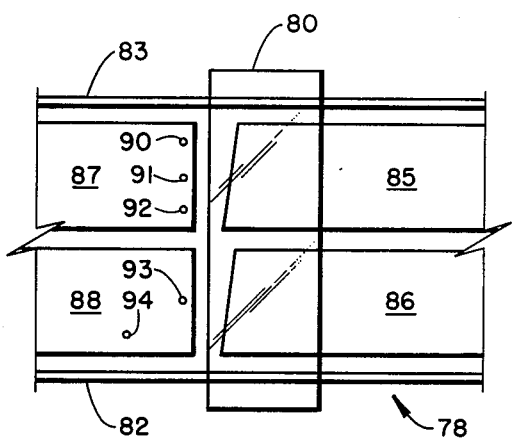
FIG. 3 is a partial top view of a segmented platen arranged in two rows in accordance with an embodiment of the present invention which can be used to apply biological markers to two discrete areas on a microscopic slide.

In FIG. 3 another platen (78) is shown. Slide (80) is shown resting on rails (82) and (83) straddling platen segments (85) and (86). Platen segment (87) is shown having three transversely aligned orifices (90), (91) and (92), and platen segment (88) is shown having two orifices (93) and (94), which are longitudinally and transversely offset from each other.

Figure 4:
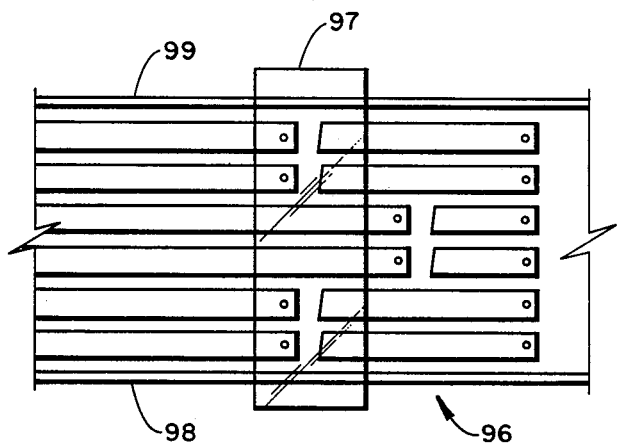
FIG. 4 is a partial top view of a segmented platen in accordance with an embodiment of the present invention which can be used to apply biological markers to as many as six discrete areas on a microscopic slide.

FIG. 4 illustrates a six row platen (96) in which glass slide (97) is shown straddling rails (98) and (99).

Figure 5:
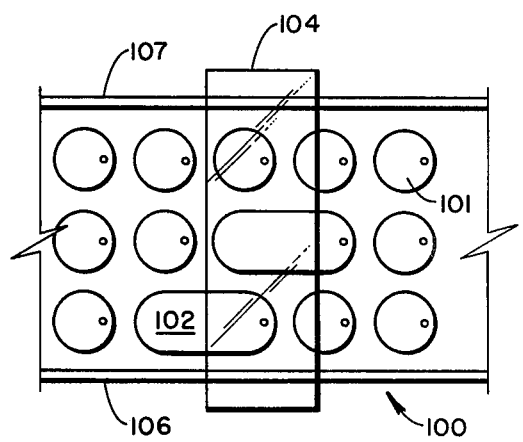
FIG. 5 is a partial top view of a segmented platen in accordance with another embodiment of the present invention in which the platen segments differ in configuration from the more or less rectangular channel segments of FIGS. 1 through 4.

In FIG. 5 a three row platen (100) is illustrated in which the platen segments, such as platen segments (101) and (102), are rounded in configuration instead of being generally rectangular in shape. Slide (104) is shown resting on suitable support members, such as rails (106) and (107).

Obviously, other configurations of the individual platen segments can be used. If desired, platen segments can cover two or more rows in certain portions of the multichannel platen. Moreover, the platen segments and channels need not be of uniform width.

It will also be understood that means other than rails can be employed for supporting flat-surfaced objects over the platen.

The platen apparatus and method of the present invention can be useful in a wide variety of different disciplines. One example is in the area of histology. Commonly, a histological examination of tissue is performed on paraffin embedded or frozen sections that are mounted on microscopic slides. The colorless tissue structure is made visible generally by staining the various cell constituents with dyes of different colors and intensities. Thus, the present invention permits the same specimen to be treated in several different areas with different monochrome stains and/or biological markers. This procedure represents a distinct advantage over the conventional use of a polychrome stain, i.e., a stain composed of a mixture of dyes. The polychrome stains which have been used in the past have the inherent weakness that, because they are a compromise prepared to achieve a combination of results, it is difficult to make the stains as specific and as free from interference as monochrome stains.

Histology provides a morphological view of tissue, and histochemistry localizes chemical substances in tissue by histochemical methods. These substances are immobilized at the site they occupy in the living tissue and are demonstrated by means of various chemicals and enzymes. A platen in accordance with the present invention permits the localization and demonstration of several components on one slide. In addition, the platen permits a combination of histostaining and histochemical treatment on one slide.

In the normal cycle of life, cells of the body are continually being exfoliated into surrounding body fluids. These shed cells are representative of the nearby organ. By separating these cells from aspirated fluids or by scraping the organ in question, cellular material is obtained which can be affixed to a microscopic slide by one of several methods. Commonly the material is affixed to a slide by either a direct smear onto the microscopic slide of an organ scraping, or the material is centrifugally prepared using a fluid aspirate. As in histology and histochemistry, these cells are stained for morphological examination or treatment with reagents for cytochemical tests to determine the state of the organ from which they were exfoliated. The platen system of the present invention permits cellular material to be treated with different biological markers on one slide for purposes of rapidly identifying the state of the organ from which cells were exfoliated and thereby avoids the necessity for conducting repeated tests on similar samples. The process of identification is thereby significantly shortened and the amount of sample required is significantly decreased.

The HEMA-TEK ® slide stainer sold by Miles Laboratories, Inc. of Elkhart, Ind. is designed for staining a blood film for cell differentiation and cellular morphology. For certain purposes, there is a need for a multirow stainer. In the area of malaria detection, particularly in asymptomatic patients or those who have the test performed during that period of time when the disease is quiescent, it is advantageous to use a combination of stains, such as the Wright, Giemsa and Acridine Orange fluorescent staining on one blood smear to confirm the presence of the plasmodium during its complete life cycle.

Other clinical disciplines in which the present invention can be effectively utilized include: immunology, serology, enzymology, virology, tissue culture, urinalysis, microbiology, parasitology, blood typing, tissue typing, chromosomal studies and the like.

From the foregoing, it will be seen that this invention is well adapted to attain all of the ends and objects hereinabove set forth, together with other advantages which are obvious and inherent. The system of the present invention retains all of the advantages of the platen method for treatment of microscopic slides over conventional immersion techniques. These advantages include the fact that only the side of the slide bearing the specimen is exposed to liquid solutions; only a minimum amount of treatment solution is required; fresh treatment solution is used for each sample; the capillary gap that maintains the treatment solution in contact with the specimen minimizes evaporation and ambient exposure; after treatment on one segment of the platen the treating solution is cleanly sheared off by surface tension as the slide is moved to another treating location, thereby minimizing cross contamination of treating solutions; and the platen is compact, lending itself to automation. Moreover, superior quality and reproducibility of results are provided because the human factor is removed, insuring uniform performance at each step.

Obviously, many modifications and variations of the invention as hereinbefore set forth can be made without departing from the spirit and scope thereof, and therefore only such limitations should be imposed as are indicated by the appended claims.

What is claimed is:

1. A platen for applying at least one liquid to discrete areas of a generally flat surfaced object moved along a predetermined path in spaced generally parallel relation above said platen, said platen comprising a plurality of spaced apart platen segments having substantially coplanar flat upper surfaces, said platen segments being arranged in at least two spaced apart rows and being provided with liquid supply orifices at selected locations in said upper surfaces thereof.

2. The platen of claim 1 in which the platen segments are of nonuniform length.

3. The platen of claim 1 in which the platen segments are part of a unitary member in which the platen segments are separated by recess portions.

4. The platen of claim 1 in which the platen segments are generally rectangular in configuration.

5. The platen of claim 1 in which the platen segments are arranged in two spaced rows and liquid supply orifices are present in each row for applying different biological marker liquid to discrete areas of a generally flat surfaced object.

6. The platen of claim 1 in which the platen segments are arranged in two spaced rows and liquid supply orifices are present in each row for applying the same biological marker to discrete areas of a generally flat surfaced object.

7. The platen of claim 1 in which the platen segments are arranged in three spaced rows and liquid supply orifices are present in each row for applying different biological marker liquid to discrete areas of a generally flat surfaced object.

8. The platen of claim 1 in which the platen segments are arranged in three spaced rows and liquid supply orifices are present in each row for applying the same biological marker to discrete areas of a generally flat surfaced object.

9. The platen of claim 1 in which the platen segments are arranged in four spaced rows and liquid supply orifices are present in each row for applying different biological marker liquid to discrete areas of a generally flat surfaced object.

10. The platen of claim 1 in which the platen segments are arranged in four spaced rows and liquid supply orifices are present in each row for applying the same biological marker to discrete areas of a generally flat surfaced object.

* * * * *